United States Patent
McCarty et al.

(10) Patent No.: US 6,344,444 B1
(45) Date of Patent: Feb. 5, 2002

(54) ARGININE-SILICATE-INOSITOL COMPLEX AND USE THEREOF

(75) Inventors: Mark F. McCarty; Jan Zielinski, both of San Diego, CA (US)

(73) Assignee: Nutrition 21, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/730,895

(22) Filed: Dec. 5, 2000

Related U.S. Application Data

(63) Continuation of application No. 09/367,267, filed as application No. PCT/US98/02443 on Feb. 11, 1998, now Pat. No. 6,156,735, which is a continuation of application No. 08/799,784, filed on Feb. 12, 1997, now Pat. No. 5,707,970.

(51) Int. Cl.$^7$ ...................... A61K 31/70; A61K 31/695; A61K 31/195
(52) U.S. Cl. ........................... 514/23; 514/63; 514/565
(58) Field of Search ........................... 514/23, 63, 565; 536/121; 562/561; 556/9

(56) References Cited

U.S. PATENT DOCUMENTS

| | | | |
|---|---|---|---|
| 3,337,403 A | 8/1967 | Zentner | |
| 4,297,349 A | 10/1981 | Barcza | |
| 4,385,052 A | 5/1983 | Zackheim et al. | |
| 5,250,569 A | 10/1993 | Godfrey | |
| 5,622,980 A | 4/1997 | Caldwell et al. | |
| 5,707,970 A | 1/1998 | McCarty et al. | |
| 6,156,735 A | * 12/2000 | McCarty et al. | ............... 514/23 |

FOREIGN PATENT DOCUMENTS

| | | |
|---|---|---|
| FR | 2745498 | 9/1997 |
| FR | 2610522 | 8/1998 |

OTHER PUBLICATIONS

Bassler, T.J., Hard water, food fibre, and silicon, *British Medical Journal* 1:919 (1978).
Calver, et al., Effect of local intra–arterial N$^G$–monomethyl–L–arginine in patients with hypertension: the nitric oxide dilator mechanism appears abnormal, *J. of Hypertension* 10:1025–1031 (1992).
Carlisle, E.M., Silicon: An Essential Element for the Chick, *Science* 178:619–621 (1972).
Carlisle, E.M., In vivo Requirement for Silicon in Articular Cartilage and Connective Tissue Formation in the Chick, *J. Nutr.* 106:478–484 (1976).
Chen, P.Y., et al., L–Arginine Abrogates Salt–sensitive Hypertension in Dah/Rapp Rats, *J. Clin. Invest.*88:1559–1567 (1991).
Clarkson, et al., Oral L–Arginine Improves Endothelium––dependent Dilation in Hypercholesterolemic Young Adults, *J. Clin. Invest.*97(8):1989–1994 (1996).

Clowes, et al., Suppression by heparin of smooth muscle cell proliferation in injured arteries, *Nature* 265:625–626 (1977).
Cooke, et al., Is NO an Endogenous Antiatherogenic Molecule, *Arteriosclerosis and Thrombosis* 14(5):653–655 (1994).
Creager, et al., L–Arginine Improves Endothelium–dependent Vasodilation in Hypercholesterolemic Humans,*J. Clin. Invest.* 90:1248–1253 (1992).
Curtis, et al., Nitric oxide supplementation or synthesis block–which is the better approach to treatment of heart disease?,*Trends in Pharmacological Sciences* 18(7):239–244 (1997).
Drexler, et al., Correction of endothelial dysfunction in coronary microcirculation of hypercholesterolaemic patients by L–arginine, *Lancet* 338:1546–1550 (1991).
Edelman, et al., Effect of controlled adventitial heparin delivery on smooth muscle cell proliferation following endothelial injury, *Proc. Natl. Acad. Sci. USA* 87:3773–3777 (1990).
Garson, et al., *Organosilicon Entities as Prophylactic and Therapeutic Agents, J. of Pharmaceutical Sciences*60(8):1113–1127 (1971).
Guyton, et al., Inhibition of Rat Aterial Smooth Muscle Cell Proliferation by Heparin . . . , *Circ. Res.* 46:625–634 (1980).
Laurant, et al., Dietary L–Arginine Attenuates Blood Pressure in Mineralocorticoid–Salt Hypertensive Rats, *Clin. and Exper. Hypertension* 17(7):1009–1024 (1995).
Loeper, et al., The Antiatheromatous Action of Silicon, *Atherosclerosis* 33:397–408 (1979).
Loeper, et al., The Physiological Role of the Silicon and its Antiatheromatous Action, in Biochemistry of Silicon and Related Problems, Bendz G. et al. Eds..Plenum Press, NY 281–296 (1978).
Luscher, T.F., Endothelium–derived nitric oxide: The endogenous nitrovasodilator in the human cardiovascular system, *Eur. Heart J.* , 12(Suppl. E):2–11 (1991).
Maulik, et al., Nitric Oxide signaling in ischemic heart, *Cardiovasc. Res.* 30(4):593–601 (1995).
Moncada, et al., The L–Arginine–Nitric Oxxide Pathway, *The New. Engl. J. of Med.* 329(27):2002–2012 (1993).
Parr, R.M., Silicon, Wine, and the Heart, *Lancet* p. 1087 1980.
Rubanyi, M.D., Ph.D., Endothelium–Derived Vasoactive Factors in Health and Disease, in Cardiovascular Significance of Endothelium–Derived Vasoactive Factors, Rubanyi, G.M., ed., Futura Publishing Company, Inc., NY xi–xix.
Schwarz, et al., Growth–promoting Effects of Silicon in Rats, *Nature* 239:333–334 (1972).

(List continued on next page.)

*Primary Examiner*—Raymond Henley, III

(57) ABSTRACT

The present invention is directed to an arginine-silicate complex and its use in the prevention and treatment of atherosclerosis, as a dietary supplement, and for promotion of structural integrity of bones and cartilage.

20 Claims, No Drawings

OTHER PUBLICATIONS

Schwarz, K., Silicon, Fibre, and Atherosclerosis, *Lancet* 454–457 (1977).

Schwarz, et al., Inverse Relation of Silicon in Drinking Water and Atherosclerosis in Finland, *Lancet* 538–539 (1977).

Schwarz, K., Significance and Functions of Silicon in Warm–Blooded Animals, in Biochemistry of Silicon and Related Problems, Bendz, G. et al., Eds., Plenum Press, NY 207–230 (1978).

Svehla, G., Reaction of Silicates, *Vogels Textbook of Macro and Semimicro Qualitative Inorganic Analysis $5^{th}$ Edition*, Longman, London pp. 350–353 (1979).

Tsao, et al., *Enhanced endothelial adhesiveness in hypercholesterolemia is attenuated by L–arginine, Circulation* 89(5):2176–2182 (1994).

\* cited by examiner

ARGININE-SILICATE-INOSITOL COMPLEX AND USE THEREOF

RELATED APPLICATIONS

This application is a continuation of U.S. patent application Ser. No. 09/367,267, filed on Dec. 13, 1999, now U.S. Pat. No. 6,156,735, which is a 371 of PCT/US98/02443, filed on Feb. 11, 1998, which is a continuation of U.S. patent application Ser. No. 08/799,784, filed on Feb. 12, 1997, now U.S. Pat. No. 5,707,970.

FIELD OF THE INVENTION

The present invention relates to an arginine silicate complex and its use in the prevention and treatment of atherosclerosis, as a dietary supplement and for promotion of structural integrity of bones and cartilage.

BACKGROUND OF THE INVENTION

Atherosclerosis is a complex and chronic disease involving the gradual accumulation of lipids, collagen, elastic fibers and proteoglycans in the arterial wall. Current methods of managing atherosclerosis include a low-fat diet, exercise and various cholesterol-lowering drugs. Although these methods can significantly retard the progression of atherosclerosis, they are not entirely satisfactory.

Heparin sulfate proteoglycans (HSPGs) produced by vascular endothelium are believed to retard the migration, multiplication and phenotypic transition of vascular smooth muscle cells, events which play a central role in the atherogenic process, and to maintain an anticoagulant luminal surface by binding and activating antithrombin III (Clowes et al., *Nature*, 265:625–626, 1977; Guyton et al., *Circ. Res.*, 46:625–634, 1980; Edelman et al., *Proc. Natl. Acad. Sci. U.S.A.*, 87:3773–3777, 1990).

Various silicon compounds administered orally or parenterally have been demonstrated to inhibit cholesterol-induced intimal hyperplasia (atherosclerosis) in rabbits (Loeper et al., *Athersclerosis*, 33:397–408, 1979: Loeper et al., in *Biochemistry of Silicon and Related Problems*, Plenum Press, New York, 1978, pp. 281–296; Garson et al., *J. Pharm. Sci.*, 60:1113–1127, 1971). The injection or ingestion of nutritionally available silicon compounds (i.e. monomethyltrisilanol, lysine silicate, sodium silicate) prevented the characteristic intimal thickening and fragmentation of arterial elastic fibers observed in atherosclerosis. Additionally, several epidemiological studies report that increased dietary intakes of silicon are associated with a reduced risk of coronary heart disease in humans (Schwarz et al., *Lancet*, i:454–457, 1977; Schwarz et al., *Lancet*, i:538–539, 1977; Bassler, *Brit. Med. J.*, 1:919, 1978; Parr, *Lancet*, i:1087, 1980).

Studies in growing young rats and chicks show that severe dietary silicon deficiency results in abnormal bone and joint structures, apparently due to subnormal production of collagen and mucopolysaccharides (Carlisle, *J. Nutr.* 106:478.484, 1976; Carlisle, *J. Nutr.* 110:1046–1055, 1980). Silicon promotes the synthesis of collagen and mucopolysaccharides in vitro (Carlisle et al., *Fed. Proc.* 37:404, 1978; Carlisle et al., *Fed. Proc.* 39:787, 1980). The biochemical method by which silicon achieves this effect are unknown. Silicone has been shown to enhance bone mineral density. When an organosilicon compound (monomethyltrisilanol) was administered to postmenopausal women by injection at a dose of 50 mg twice weekly, femoral density increased significantly by an average of 4.7% over 14 months of administration (Eisinger et al., *Magnesium Res.* 6:247–249, 1993). In ovariectomized rats, oral orthosilicic acid slowed bone turnover and increased the bone formation rate (Hott et al., *Calcif. Tissue Int.* 53:174–179, 1993).

Bone and cartilage are dynamic tissues in both juvenile and adult animals. In bone, osteoclasts solubilize the hydroxyapatite bone matrix and degrade collagen, whereas osteoblasts concurrently rebuild bone through collagen synthesis and hydroxyapatite deposition. Analogously, chondrocytes in cartilage simultaneously degrade the collagen and proteoglycan matrix and resynthesize it. The impact of silicone on bone and cartilage formation in adult animal is essentially unknown. However, it is highly unlikely that the role of silicon in bone and cartilage metabolism is limited to juvenile animals.

The nutritional role of silicon is to support adequate synthesis of mucopolysaccharides, proteoglycans and collagen (Schwarz et al., *Nature*, 239:333–334, 1972; Carlisle, *Science*, 178:619621, 1972; Carlisle, *J. Nutr.*, 106:478–484, 1976; Schwarz, in *Biochemistry of Silicon and Related Problems*, Plenum Press, New York, 1978, pp. 207–230). Optimal silicon nutrition may promote production of protective HSPGs by endothelial cells.

Arginine, an essential amino acid, is the biosynthetic precursor for the nitric oxide (NO) produced by vascular endothelium (Moncada, *New Engl. J. Med.*, 329:2002–2012, 1993). NO exerts vasodilatory, antiatherosclerotic and antithrombotic effects, and deficient endothelial production of NO may play a prominent pathogenic role in atherosclerosis, hypertension and diabetes (Calver et al., *J. Hypertension*, 10:1025–1031, 1992; Cooke et al., *Arterioscler. Thromb.*, 14:653–655, 1994; Rubanyi, in: *Cardiovascular Significance of Endothelium-Derived Vasoactive Factors*, Futura Publishing Co, Inc., New York, 1991, pp. xi–xix). In some though not all clinical studies, parenteral or oral administration of arginine has enhanced vascular NO synthesis (Drexler et al., *Lancet*, 338:1546–1550, 1991). In animal models of hypertension, arginine supplementation has moderated the increase in blood pressure (Chen et al., *J. Clin. Invest.*, 88:1559–1567, 1991; Laurant et al., *Clin. Exp. Hyperten.*, 17:1009–1024, 1995). Thus, under at least some circumstances, arginine availability can be rate-limiting for NO production. A recently published clinical study indicates that oral arginine can enhance endothelium-dependent relaxation in hypercholesterolemic young people (Creager et al., *J. Clin. Invest.*, 90:1248–1253, 1992; Clarkson et al., *J. Clin. Invest.*, 97:1989–1994, 1996) which is indicative of increased efficiency of vascular NO production.

There is a constant need for therapeutic/prophylactic agents capable of preventing or retarding the progression of atherosclerosis and promoting the formation of bone and cartilage. The present invention addresses these needs.

SUMMARY OF THE INVENTION

One embodiment of the present invention is a method of making an arginine-silicate-inositol complex comprising the steps of:

(a) combining arginine, a silicate salt and inositol to form a suspension;

(b) heating the suspension to promote gel formation;

(c) allowing the gel to crystallize;

(d) mixing the crystals formed in step (c) with an alcohol to promote crystallization; and (e) collecting the crystals formed in step (d). Preferably, the silicate salt is potassium silicate. Advantageously, the heating is performed at about 95° C. The method may further comprise repeating step (d) prior to collecting the crystals. In one aspect of this preferred embodiment, the crystals are collected by filtration. Preferably, the crystallization-promoting alcohol is ethanol.

The present invention also provides an arginine-silicate-inositol complex formed by the method described above.

Another embodiment of the invention is a method for preventing or inhibiting atherosclerosis in a mammal, preferably a human, comprising the step of administering to the mammal an effective atherosclerosis-preventing or inhibiting amount of the arginine-silicon-inositol complex described above. Preferably, the administering step is parenteral or oral. Advantageously, the effective amount is between about 250 mg and about 2,500 mg; more advantageously, the effective amount is between about 500 mg and about 1,000 mg. For the average 70 kg man, this equals a dosage of between about 3.6 and 14 mg/kg (250–2, 600 mg) and between about 7.1 mg/kg and 14 mg/kg (500 mg–1,000 mg), respectively.

Still another embodiment of the invention is a method for supplementing dietary arginine comprising administering to an individual the complex described above.

The present invention also provides an arginine-silicate-inositol complex, wherein the ratio of arginine to silicate to inositol is about 3:3:1.

Another embodiment of the present invention is the use of the arginine-silicon-inositol complex described above for supplementing dietary arginine.

The present invention also provides the use of the arginine-silicon-inositol complex described above for the prevention or inhibition of atherosclerosis.

Another embodiment of the invention is a method for preventing bone demineralization or cartilage degradation in an individual in need thereof, comprising administering to the individual an effective bone demineralization or cartilage degradation-inhibiting amount of the arginine silicate complex described above.

Yet another embodiment of the invention is the use of the arginine silicate complex described above for preventing bone demineralization or cartilage degradation in an individual. Preferably, the administering route is parenteral or oral.

The present invention also provides a method for treating a bone or cartilage disorder in an individual in need thereof, comprising administering to the individual an effective amount of the arginine silicate complex described above. In one aspect of this preferred embodiment, the bone disorder is osteoporosis, osteogenesis imperfecta or bone fractures. Preferably, the cartilage disorder is osteoarthritis, inflammatory arthritis, a torn tendon or a torn ligament. Advantageously, the administration is parenteral or oral.

Still another embodiment of the invention is the use of the arginine silicate complex described above for treating a bone or cartilage disorder in an individual.

Another embodiment of the invention is a bone demineralization opposing and cartilage degradation inhibiting pharmaceutical formulation, comprising a therapeutically effective amount of the arginine silicate complex described above; and a pharmaceutically acceptable carrier or diluent therefor.

The present invention also provides a method of treating a mammal to alleviate the pathological effects of osteoporosis, osteogenesis imperfecta, bone fractures, osteoarthritis, inflammatory arthritis and other disorders of bone and cartilage, wherein the method comprises administering to said mammal the arginine silicate complex described above, wherein said complex is administered to the mammal in an amount sufficient to oppose bone demineralization and to inhibit cartilage degradation.

DETAILED DESCRIPTION OF THE PREFERRED EMBODIMENTS

The present invention provides an arginine silicate complex produced by combining arginine, a silicate salt and inositol, a method for its synthesis and its uses as a nutritional supplement, for the prevention and treatment of atherosclerosis and for promoting the structural integrity of bone and cartilage. Although the product described herein contains arginine, silicate and inositol, it is referred to throughout the specification as "arginine silicate."

Arginine silicate is synthesized by reacting arginine (free base), potassium silicate and inositol as described in Example 1. The resulting complex is completely soluble and provides silicate in a bioavailable form which will have good nutritional availability. Silicates are typically insoluble in aqueous solutions. However, the use of inositol in the synthesis of the arginine silicate-containing complex renders the complex soluble in aqueous solution. In contrast, arginine silicate synthesized in the absence of inositol was insoluble in aqueous solutions. This unexpected solubilization effect of inositol is of paramount importance to the use of the complex as a bioavailable source of arginine and silicate. Inositol facilitates solubilization of arginine silicate by increasing hydrogen bonding between arginine and silicic acid. Although other polyhydroxy compounds including, but not limited to, mannitol and sorbitol can also be used, inositol is preferred. The bioavailability of silicate was confirmed as described in Example 3. In a preferred embodiment, the combining molar ratio of arginine to silicate is about 1:1 and the ratio of inositol to arginine and silicate is about 1:3. Although potassium silicate was used as a reactant, the use of other silicate salts including sodium silicate and magnesium silicate, is also within the scope of the invention. The mixture resulting from the combination of inositol, silicate salt and arginine is a highly viscous suspension which is clarified by heating. In a preferred embodiment, the suspension is heated to between about 80° C. and about 100° C., more preferably about 95° C., until clarification is observed. At this time, heating and stirring is discontinued and gel formation is initiated. Crystallization of the arginine silicate complex occurs as gel formation progresses. The resulting crystal bulk is dispersed and mixed with an alcohol for about 30 min. to effect more complete crystallization and recovery of a purer product. Heavy metal content of the final product was less than 5 ppm which is considered undetectable. The level of iron was also very low (10 ppm). These findings indicate that the product is virtually free of such contaminants. Although the use of ethanol for crystallization of the arginine silicate complex is preferred, the use of other alcohols is also contemplated. Optionally, a second alcohol crystallization step may be performed. The final product, a complex containing arginine, silicate and inositol, is collected by filtration, washed and dried.

Arginine silicate may be used both as a source of the essential amino acid arginine and as a source of silicate, both of which exert antiatherosclerotic effects. The oral administration of this compound delivers arginine and silicate to appropriate sites of action. Arginine silicate is useful as a therapeutic or preventative agent for atherosclerosis and may also be given as a dietary supplement to maintain an antiatherogenic state. Thus, the administration of arginine silicate has prophylactic as well as therapeutic applications. Arginine silicate is highly soluble in water and provides good nutritional availability of both arginine and silicate. In addition to providing silicate, the arginine silicate complex is also a good dietary supplement for the essential amino acid arginine.

The arginine silicate complex of the invention promotes bone and cartilage formation in a mammal in need thereof, particularly in humans. Bioavailable nutritional silicon in the form of the arginine silicate complex described herein also increases bone density and prevents bone demineralization. In one preferred embodiment, the complex is administered prophylactically to prevent bone demineralization and cartilage degradation. One preferred use of the complex is prevention and treatment of osteoporosis which results from bone demineralization in postmenopausal women. The complex is used to prevent or treat any bone demineralization disorder, including osteoporosis and osteogenesis imperfecta. The arginine silicate complex is also used as an adjunct in the treatment of bone fractures. For example, an individual with a bone fracture is treated by casting in combination with oral administration of the arginine silicate complex of the invention to promote faster healing of the fracture. This lessens the time the individual must wear the cast in situations where a cast is applied. The arginine silicate complex can also be used to treat "green stick" fractures in which no actual separation of the bone has occurred.

In yet another preferred embodiment, The arginine silicate complex is used to treat or prevent osteoarthritis and inflammatory arthritis.

In another preferred embodiment, the arginine silicate complex is administered to an individual with torn cartilage or tendons either alone, or after surgery to repair the damaged area. By promoting cartilage formation, the arginine silicate complex lessens the recovery time after surgery.

The compounds of the invention may be administered parenterally, orally, intravenously, intraarterially, intramuscularly or in any other systemic fashion, in appropriate dosage units, as desired. The term "parenteral" used herein includes subcutaneous, intravenous, intraarterial, injection or infusion techniques, without limitation. However, oral administration is preferred. For oral administration, the compounds may be provided as a tablet, aqueous or oral suspension, dispersible powder or granule, emulsion, hard or soft capsule, syrup or elixir. Compositions intended for oral use may be prepared according to any method known in the art for the manufacture of pharmaceutical compositions and such compositions may contain one or more of the following agents: sweeteners, flavoring agents, coloring agents, preservatives, solubilizers, wetting agents, stabilizers, colorants, antioxidants, coating agents and diluents. The sweetening agents and flavoring agents will increase the palatability of the preparation. Tablets containing arginine silicate in admixture with non-toxic pharmaceutically acceptable excipients suitable for tablet manufacture are acceptable. Such excipients include inert diluents such as calcium carbonate, sodium carbonate, lactose, calcium phosphate or sodium phosphate; granulating and disintegrating agents such as corn starch or alginic acid; binding agents such as starch, gelatin or acacia; and lubricating agents such as magnesium stearate, stearic acid or talc. Tablets may be uncoated or may be coated by known techniques to delay disintegration and absorption in the gastrointestinal tract and thereby provide a sustained action over a longer period of time. For example, a time delay material such as glyceryl monostearate or glyceryl distearate alone or with a wax may be employed.

Formulations for oral use may also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, such as peanut oil, liquid paraffin or olive oil.

Aqueous suspensions may contain the compounds of the invention in admixture with excipients suitable for the manufacture of aqueous suspensions. Such excipients include suspending agents, dispersing or wetting agents, one or more preservatives, one or more coloring agents, one or more flavoring agents and one or more sweetening agents such as sucrose or saccharin.

Oil suspensions may be formulated by suspending the active ingredient in a vegetable oil, such as arachis oil, olive oil, sesame oil or coconut oil, or in a mineral oil such as liquid paraffin. The oil suspension may contain a thickening agent, such as beeswax, hard paraffin or cetyl alcohol. Sweetening agents, such as those set forth above, and flavoring agents may be added to provide a palatable oral preparation. These compositions may be preserved by an added antioxidant such as ascorbic acid. Dispersible powders and granules of the invention suitable for preparation of an aqueous suspension by the addition of water provide the active ingredient in admixture with a dispersing or wetting agent, a suspending agent and one or more preservatives. Additional excipients, for example sweetening, flavoring and coloring agents, may also be present. Syrups and elixirs may be formulated with sweetening agents such as glycerol, sorbitol or sucrose. Such formulations may also include a demulcent, a preservative, a flavoring or a coloring agent. For assistance in formulating the compositions of the present invention, one may refer to Remington's Pharmaceutical Sciences, 15th Edition, Mack Publishing Co., Easton, Pa.

The arginine silicate preparations for parenteral administration may be in the form of a sterile injectable preparation, such as a sterile injectable aqueous or oleaginous suspension. This suspension may be formulated according to methods well known in the art using suitable dispersing or wetting agents and suspending agents. The sterile injectable preparation may also be a sterile injectable solution or suspension in a non-toxic parenterally-acceptable diluent or solvent, such as a solution in 1,3-butanediol. Suitable diluents include, for example, water, Ringer's solution and isotonic sodium chloride solution. In addition, sterile fixed oils may be employed conventionally as a solvent or suspending medium. For this purpose, any bland fixed oil may be employed including synthetic mono or diglycerides. In addition, fatty acids such as oleic acid may likewise be used in the to prepare injectable preparations.

Optionally, the pharmaceutical compositions of the invention may comprise the arginine silicate complex combined with one or more compounds exhibiting a different activity, for example, an antibiotic or other pharmacologically active material.

The amount of arginine silicate that may be combined with the carrier material to produce a single dosage form will vary depending upon the host treated and the particular form of administration.

In a preferred embodiment, as a preventative or therapeutic agent for atherosclerosis or bone and cartilage disorders, arginine silicate is administered three times daily in an amount ranging from about 250 mg to about 2,500 mg. In a particularly preferred embodiment, the compounds are administered three times daily in an amount ranging from about 500 mg to about 1,000 mg. It is also contemplated that the compounds may be administered once or twice a day rather than three times, depending on the severity of the atherosclerotic lesion.

Arginine silicate was synthesized as described in the following example.

EXAMPLE 1

Preparation of Arginine Silicate

Arginine (3.8 g, 21.8 mmol) was added to a vigorously stirred solution of inositol (1.25 g, 6.9 mmol) in potassium silicate [5 ml, 29.8° Be, 8.3% $K_2O$ (0.52 g, 5.5 mmol), 20.8% $SiO_2$ (1.3 g, 21.8 mmol)], resulting in a highly viscous suspension. The suspension was heated to 95° C. Heating and stirring were discontinued when the mixture became clear and started to form a gel. The mixture was left overnight at room temperature and allowed to crystallize. The resulting crystal bulk was dispersed, mixed with ethanol (5 ml) and left for 30 minutes. This procedure was repeated with another 5 ml ethanol on the resulting crystals and left overnight to complete crystallization. The final arginine silicate product was collected by filtration, washed with ethanol and dried under vacuum. The amount of product was 7.7 g obtained as a hydrate (111% of the total mass of the used reagents.

An analytical sample kept under vacuum at 90° for 1 hour lost 11.5% of its mass due to removal of water. Elemental analysis indicated: 25.13% C, 6.24% H, 14.11% N, 8.25% Si (17.68% $SiO_2$). The potassium content (5.4%) was determined using a kit (HACH Co., Loveland Colo., Catalog No. 234394) based on the well known tetraphenylborate method. These results are in agreement with the calculated content of elements in the arginine silicate product.

EXAMPLE 2

Kinetics of Arginine Silicate Product

Studies of the kinetics in aqueous solution of the arginine silicate product indicated the formation of non-dissociable arginine silicate complex as a function of used concentration. Measurement of the ratio of dissociated to non-dissociated forms of arginine silicate was performed using a HACH kit (Catalog No. 2429600) in which the absorbance at 452 nm is a function of the concentration of silicomolybdate formed under acid conditions and expressed as % of silica ($SiO_2$). An aqueous solution of arginine silicate product (10 g/L) was diluted at the appropriate time to 0.5 g/L and the content of silica was measured using the HACH method. The level of silica at time 0 was 17.5%; at 1 hour was 11.8%; at 2 hours was 10.8%; and at 24 hours was 9.2%. In an aqueous solution of 0.5 g/l arginine silicate, the level of silica was 17.5% and was stable after 24 hours, confirming the solubility of the product.

EXAMPLE 3

Bioavailability of Arginine Silicate

A solution (8 g/l) of arginine silicate was prepared and, after donating a baseline 24-hour urine, a human volunteer consumed three one-cup servings daily for three days. On the third day, he once again obtained a 24-hour urine. Silicon assay revealed that urinary silicon output has increased more than tenfold from baseline. The amount of silicon in the third-day urine corresponded to approximately 25% of the silicon ingested daily from the arginine silicate solution. This demonstrates the good bioavailability of the silicon in solubilized arginine silicate.

While particular embodiments of the invention have been described in detail, it will be apparent to those skilled in the art that these embodiments are exemplary rather than limiting, and the true scope of the invention is that defined by the appended claims.

What is claimed is:

1. A method for supplementing dietary silicate comprising administering to an individual an arginine-silicate-inositol complex, wherein said arginine-silicate-inositol complex is formed by a method comprising the steps of:
    (a) combining arginine, a silicate salt and inositol to form a suspension; and
    (b) heating the suspension to promote gel formation.

2. The method of claim 1, wherein said arginine-silicate inositol complex is formed by a method further comprising the step of (c) allowing the gel to crystallize.

3. The method of claim 2, wherein said arginine-silicate inositol complex is formed by a method further comprising the step of (d) mixing crystals formed in step (c) with an alcohol to promote crystallization.

4. The method of claim 3, wherein said arginine-silicate inositol complex is formed by a method further comprising the step of (e) collecting the crystals formed in step (d).

5. The method of claim 1, wherein said arginine-silicate-inositol complex is administered parenterally or orally.

6. A method of promoting bone and cartilage formation comprising administering to an individual an effective bone and cartilage formation promoting amount of an arginine-silicate-inositol complex, wherein said arginine-silicate-inositol complex is formed by a method comprising the steps of:
    (a) combining arginine, a silicate salt and inositol to form a suspension; and
    (b) heating the suspension to promote gel formation.

7. The method of claim 6, wherein said arginine-silicate-inositol complex is formed by a method further comprising the step of (c) allowing the gel to crystallize.

8. The method of claim 7, wherein said arginine-silicate-inositol complex is formed by a method further comprising the step of (d) mixing the crystals formed in step (c) with an alcohol to promote crystallization.

9. The method of claim 8, wherein said arginine-silicate-inositol complex is formed by a method further comprising the step of (e)collecting the crystals formed in step (d).

10. The method of claim 6, wherein said arginine-silicate-inositol complex is administered parenterally or orally.

11. The method of claim 6, wherein said effective amount is between about 250 mg and about 2,500 mg.

12. The method of claim 6, wherein said effective amount is between about 500 mg and about 1,000 mg.

13. A method of increasing bone density in an individual in need thereof comprising the step of administering to said individual an effective bone density-increasing amount of an arginine-silicate-inositol complex, wherein said complex is formed by a method comprising the steps of:
    (a) combining arginine, a silicate salt and inositol to form a suspension; and
    (b) heating the suspension to promote gel formation.

14. The method of claim 13, wherein said complex is formed by a method further comprising the step of (c) allowing the gel to crystallize.

15. The method of claim 14, wherein said complex is formed by a method further comprising the step of (d) mixing the crystals formed in step (c) with an alcohol to promote crystallization.

16. The method of claim 15, wherein said complex is formed by a method further comprising the step of (e) collecting the crystals formed in step (d).

17. A method of promoting the healing of a bone fracture comprising administering to an individual an arginine-silicate-inositol complex, wherein said arginine-silicate-inositol complex is formed by a method comprising the steps of:
(a) combining arginine, a silicate salt and inositol to form a suspension; and
(b) heating the suspension to promote gel formation.

18. The method of claim 17, wherein said arginine-silicate-inositol complex is formed by a method further comprising the step of (c) allowing the gel to crystallize.

19. The method of claim 18, wherein said arginine-silicate-inositol complex is formed by a method further comprising the step of (d) mixing the crystals formed in step (c) with an alcohol to promote crystallization.

20. The method of claim 19, wherein said arginine-silicate-inositol complex is formed by a method further comprising the step of (e) collecting the crystals formed in step (d).

* * * * *